(12) United States Patent
Moore

(10) Patent No.: US 7,069,191 B1
(45) Date of Patent: Jun. 27, 2006

(54) METHODS FOR REDUCING THE SUSCEPTIBILITY OF A PEAK SEARCH TO SIGNAL NOISE

(75) Inventor: Douglas E. Moore, Round Rock, TX (US)

(73) Assignee: Luminex Corporation, Austin, TX (US)

( * ) Notice: Subject to any disclaimer, the term of this patent is extended or adjusted under 35 U.S.C. 154(b) by 0 days.

(21) Appl. No.: 10/913,030

(22) Filed: Aug. 6, 2004

Related U.S. Application Data

(60) Provisional application No. 60/492,941, filed on Aug. 6, 2003.

(51) Int. Cl.
*H04B 15/00* (2006.01)

(52) U.S. Cl. ...................... 702/191; 356/400
(58) Field of Classification Search ............ 702/20–22, 702/27, 28, 30, 32, 49, 175, 180, 183, 191, 702/195; 356/400, 427, 433; 422/68.1
See application file for complete search history.

(56) References Cited

U.S. PATENT DOCUMENTS

| | | | | |
|---|---|---|---|---|
| 5,067,090 A | | 11/1991 | Seeman ........................ 702/8 |
| 5,365,343 A | * | 11/1994 | Knapp ........................ 356/427 |
| 5,367,474 A | * | 11/1994 | Auer et al. .................. 702/21 |
| 5,736,330 A | | 4/1998 | Fulton ........................... 435/6 |
| 5,768,412 A | * | 6/1998 | Mitsuyama et al. ........ 382/173 |
| 5,844,685 A | * | 12/1998 | Gontin ........................ 356/433 |
| 5,981,180 A | | 11/1999 | Chandler et al. .............. 435/6 |
| 6,046,807 A | | 4/2000 | Chandler ..................... 356/318 |
| 6,057,107 A | | 5/2000 | Fulton ........................... 435/6 |
| 6,139,800 A | | 10/2000 | Chandler ................. 422/82.08 |
| 6,268,222 B1 | | 7/2001 | Chandler et al. ........... 436/523 |
| 6,366,354 B1 | | 4/2002 | Chandler ..................... 356/318 |
| 6,411,904 B1 | | 6/2002 | Chandler ..................... 702/21 |
| 6,449,562 B1 | | 9/2002 | Chandler et al. ............. 702/19 |
| 6,514,295 B1 | | 2/2003 | Chandler et al. .............. 8/607 |
| 6,524,793 B1 | | 2/2003 | Chandler et al. ............. 435/6 |
| 6,528,165 B1 | | 3/2003 | Chandler ................. 428/402.2 |
| 6,563,583 B1 | * | 5/2003 | Ortyn et al. ................ 356/400 |
| 6,592,822 B1 | | 7/2003 | Chandler ................. 422/82.05 |
| 6,630,299 B1 | * | 10/2003 | Carrion et al. ................. 435/5 |

* cited by examiner

*Primary Examiner*—Marc S. Hoff
*Assistant Examiner*—Mohamed Charioui
(74) *Attorney, Agent, or Firm*—Charles D. Huston; Ann Marie Mewherter; Daffer McDaniel, LLP

(57) ABSTRACT

A method to minimize noise is used to analyze data generated from a measurement system such as a flow cytometer. One embodiment of a computer-implemented method includes determining sums of different subsets of sample values. The method also includes determining the subset of the sample values having the largest sum. In addition, the method includes designating the subset of the sample values having the largest sum as a peak sum of the sample values. Such a peak sum minimizes the impact of noise leading to better determinations of particle identity, reaction identity, and the like.

16 Claims, 3 Drawing Sheets

15 # METHODS FOR REDUCING THE SUSCEPTIBILITY OF A PEAK SEARCH TO SIGNAL NOISE

PRIORITY APPLICATION

This application claims benefit of provisional application No. 60/492,941 entitled "Methods for Reducing the Susceptibility of a Peak Search to Signal Noise," filed Aug. 6, 2003.

BACKGROUND OF THE INVENTION

1. Field of the Invention

This invention generally relates to methods for reducing the susceptibility of a peak search to signal noise. Certain embodiments relate to determining a peak value of a pulse based on the largest sum of sample values rather than the largest sample value.

2. Description of the Related Art

Generally, flow cytometers provide measurements of fluorescence intensity of laser excited polystyrene beads as they pass linearly through a flow chamber. In some systems, there are four measurements that are performed: the level of light scattered by a bead at 90 degrees to the excitation source, two measurements of fluorescence used to determine the bead "identity," and a third fluorescence measurement typically used to quantify a chemical reaction of interest. Each of the three fluorescent measurements is made at a different wavelength.

In applications such as flow cytometry, the detectors generate a number of output signals or "samples" that make up a single pulse. Each pulse is generally attributable to one event such as, in the case of flow cytometry, illumination of one bead. As the event progresses, the light measured from scattering and/or fluorescence emission by the bead increases as the bead enters the beam of light, reaches a maximum at the center of the beam, and tapers to a nominal value as it leaves the beam. In this manner, a number of output signals will be generated over time, and the samples which make up each individual pulse may be determined. Generally, identifying the samples which belong to a single pulse involves determining a peak value of the pulse. A number of samples occurring before and after the peak value is then summed.

However, there are several disadvantages to the current methods for determining the peak value of the pulse. For example, a peak value is generally determined by identifying the largest sample in a set of samples. The pulse is assumed to be symmetrical about the peak value. A predetermined number of samples occurring before and after the peak value are then summed. However, when a signal being digitized includes noise, it is possible that a noise spike in the vicinity of the desired pulse may be misidentified as the pulse peak value thereby causing the summation to include incorrect sample data (i.e., samples that are actually baseline values).

Accordingly, it may be advantageous to develop a method for identifying the peak value of a pulse, which may or may not include noise, such that the summation may accurately reflect the pulse.

SUMMARY OF THE INVENTION

The present invention relates to various computer-implemented methods that may be used to analyze data generated from a measurement system such as a flow cytometer. Although the methods are described herein with respect to flow cytometry, it is to be understood that these methods may also be used to analyze measurement data obtained using other techniques as well. One embodiment of a computer-implemented method includes determining sums of different subsets of sample values. The method also includes determining the subset of the sample values having the largest sum. In addition, the method includes designating the subset of the sample values having the largest sum as a peak sum of the sample values that make up a single pulse. Therefore, the peak sum is designated as the sum for the single pulse. As such, the peak sum is a measure of the light scattered or emitted by a microsphere. The peak sum may be used to determine an identity of the microsphere, a size of the microsphere, and/or a reaction taking place on the surface of the microsphere. The method may include any other steps of any other methods described herein.

In one aspect, the invention contemplates a digital sampling and processing methodology to mitigate noise in one or more samples. As particles are flowing in a flow cytometer, each particle is illuminated and the scattered or emitted light is detected. The detection output signals are converted to digital samples and grouped into a plurality of subsets. Each sum of subsets are summed and the sums compared, whereupon the greatest sum is designated as the sum for the event. By this process, the effects of noise are minimized.

In another aspect, the invention contemplates a flow cytometer having a signal processor which groups digital sample values and determines a sum for each group. The group sums are compared and the greatest sum is designated as the peak sum for a particle illumination.

BRIEF DESCRIPTION OF THE DRAWINGS

Other objects and advantages of the invention will become apparent upon reading the following detailed description and upon reference to the accompanying drawings in which.

Figure 1:
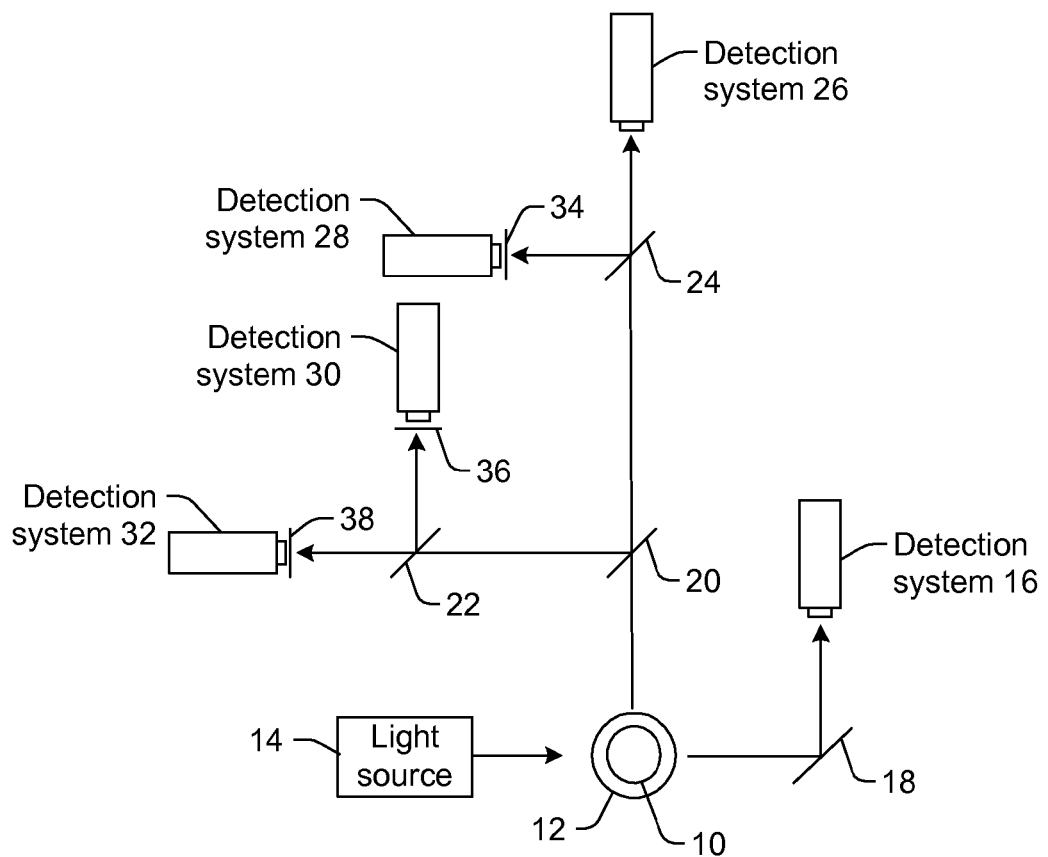
FIG. 1 is a schematic diagram illustrating one example of a measurement system that may be used to carry out the methods described herein.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Although the embodiments are described herein with respect to microspheres or polystyrene beads, it is to be understood that the measurement systems and methods may also be used with microparticles, beads, microbeads, latex particles, latex beads, fluorescent beads, fluorescent particles, colored particles, colored beads, and cells. The microspheres may serve as vehicles for molecular reactions. Examples of appropriate microspheres, beads, and particles are illustrated in U.S. Pat. No. 5,736,330 to Fulton, U.S. Pat. No. 5,981,180 to Chandler et al., U.S. Pat. No. 6,057,107 to Fulton, U.S. Pat. No. 6,268,222 to Chandler et al., U.S. Pat. No. 6,449,562 to Chandler et al., U.S. Pat. No. 6,514,295 to Chandler et al., U.S. Pat. No. 6,524,793 to Chandler et al., and U.S. Pat. No. 6,528,165 to Chandler, which are incorporated by reference as if fully set forth herein. The measurement systems and methods described herein may be used with any of the microspheres, beads, and particles described in these patents. In addition, microspheres for use in flow cytometry may be obtained from manufacturers such as Luminex Corp., Austin, Tex. The terms "beads" and "microspheres" are used interchangeably herein.

Turning now to the drawings, FIG. 1 illustrates one example of a measurement system that may be used to perform the methods described herein. It is noted that FIG. 1 is not drawn to scale. In particular, the scale of some of the elements of the figure are greatly exaggerated to emphasize characteristics of the elements. Some elements of the measurement system such as a digital signal processor (DSP) have not been included in the figure for the sake of clarity.

In FIG. 1, the measurement system is shown along a plane through the cross-section of cuvette 12 through which microspheres 10 flow. In one example, the cuvette may be a standard quartz cuvette such as that used in standard flow cytometers. Any other suitable type of viewing or delivery chamber, however, may also be used to deliver the sample for analysis. The measurement system includes light source 14. Light source 14 may include any appropriate light source known in the art such as a laser. The light source may be configured to emit light having one or more wavelengths such as blue light or green light. Light source 14 may be configured to illuminate the microspheres as they flow through the cuvette. The illumination may cause the microspheres to emit fluorescent light having one or more wavelengths or wavelength bands. In some embodiments, the system may include one or more lenses (not shown) configured to focus light from the light source onto the microspheres or the flowpath. The system may also include more than one light source. In one embodiment, the light sources may be configured to illuminate the microspheres with light having different wavelengths or wavelength bands (e.g., blue light and green light). In some embodiments, the light sources may be configured to illuminate the microspheres at different directions.

Light scattered forwardly from the microspheres may be directed to detection system 16 by folding mirror 18 or another such light directing component. Alternatively, detection system 16 may be placed directly in the path of the forwardly scattered light. In this manner, the folding mirror or other light directing components may not be included in the system. In one embodiment, the forwardly scattered light may be light scattered by the microspheres at an angle of about 180 degrees from the direction of illumination by light source 14, as shown in FIG. 1. The angle of the forwardly scattered light may not be exactly 180 degrees from the direction of illumination such that incident light from the light source may not impinge upon the photosensitive surface of the detection system. For example, the forwardly scattered light may be light scattered by the microspheres at angles less than or greater than 180 degrees from the direction of illumination (e.g., light scattered at an angle of about 170 degrees, about 175 degrees, about 185 degrees, or about 190 degrees).

Light scattered and/or emitted by the microspheres at an angle of about 90 degrees from the direction of illumination may also be collected. In one embodiment, this scattered light may be separated into more than one beam of light by one or more beamsplitters or dichroic mirrors. For example, light scattered and/or emitted at an angle of about 90 degrees to the direction of illumination may be separated into two different beams of light by beamsplitter 20. The two different beams of light may be separated again by beamsplitters 22 and 24 to produce four different beams of light. Each of the beams of light may be directed to a different detection system, which may include one or more detectors. For example, one of the four beams of light may be directed to detection system 26. Detection system 26 may be configured to detect light scattered by the micro spheres.

Scattered light detected by detection system 16 and/or detection system 26 may generally be proportional to the volume of the microspheres that are illuminated by the light source. Therefore, output signals of detection system 16 and/or output signals of detection system 26 may be used to determine a diameter of the microspheres that are in the illumination zone or detection window. In addition, the output signals of detection system 16 and/or detection system 26 may be used to identify two or more microspheres that are stuck together or that are passing through the illumination zone at approximately the same time.

The other three beams of light may be directed to detection systems 28, 30, and 32. Detection systems 28, 30, and 32 may be configured to detect fluorescence emitted by the microspheres. Each of the detection systems may be configured to detect fluorescence of a different wavelength or a different range of wavelengths. For example, one of the detection systems may be configured to detect green fluorescence. Another of the detection systems may be configured to detect yellow-orange fluorescence, and the other detection system may be configured to detect red fluorescence.

In some embodiments, spectral filters 34, 36, and 38 may be coupled to detection systems 28, 30, and 32, respectively. The spectral filters may be configured to block fluorescence of wavelengths other than that which the detection systems are configured to detect. In addition, one or more lenses (not shown) may be optically coupled to each of the detection systems. The lenses may be configured to focus the scattered light or emitted fluorescence onto a photosensitive surface of the detectors.

In some embodiments, the output signals generated from fluorescence emitted by the microspheres may be used to determine an identity of the microspheres and information about a reaction taking place on the surface of the microspheres. For example, output signals of two of the detection systems may be used to determine an identity of the microspheres, and output signals of the other detection system may be used to determine a reaction taking place on the surface of the microspheres. Therefore, the selection of the detectors and the spectral filters may vary depending on the type of dyes incorporated into or bound to the microspheres and/or the reaction being measured (i.e., the dye(s) incorporated into or bound to the reactants involved in the reaction).

The detection systems that are used to determine an identity of the sample microspheres (e.g., detection systems 28 and 30) may be avalanche photodiodes (APDs) or any other suitable detector known in the art. The detection system that is used to identify a reaction taking place of the surface of the microspheres (e.g., detection system 32) may be a photo-multiplier tube (PMT) or any other suitable detector known in the art.

Although the system of FIG. 1 is shown to include two detection systems having two different detection windows for distinguishing between microspheres having different dye characteristics, it is to be understood that the system may include more than two such detection windows (i.e., 3 detection windows, 4 detection windows, etc.). In such embodiments, the system may include additional beamsplitters and additional detection systems having other detection windows. In addition, spectral filters and/or lenses may be coupled to each of the additional detection systems.

In another embodiment, the system may include two or more detection systems configured to distinguish between different materials that are reacted on the surface of the microspheres. The different reactant materials may have dye characteristics that are different than the dye characteristics of the microspheres.

Additional examples of measurement systems that may be used to perform the methods described herein are illustrated in U.S. Pat. No. 5,981,180 to Chandler et al., U.S. Pat. No. 6,046,807 to Chandler, U.S. Pat. No. 6,139,800 to Chandler, U.S. Pat. No. 6,366,354 to Chandler, U.S. Pat. No. 6,411,904 to Chandler, U.S. Pat. No. 6,449,562 to Chandler et al., U.S. Pat. No. 6,524,793 to Chandler et al., and U.S. Pat. No. 6,592,822 to Chandler, which are incorporated by reference as if fully set forth herein. The measurement system described herein may also be further configured as described in these patents.

The rate of sampling of the measurement system may be selected by the user. For example, the rate of sampling may be about one million sampling periods per second, which may be increased or decreased. Typically, a fixed rate of oversampling is used that creates about 8–12 sampling periods per average event, with a maximum of about 20 sampling moments per event. However, more or less values may be used for different applications; for example, when there is a complex or broad, multi-peak fluorescence emission spectrum, more than 50 or 100 sampling periods per event may be specified.

During a sample period, the detectors (e.g., 16, 26, 28, 30, or 32 in FIG. 1) sample and measure light parameters. The detector's output current is generally proportional to the fluorescent or scattered light impinging on it and results in a current. The current may be converted to a voltage, low pass filtered, and then digitized by an A/D converter. Digitized data from the detectors may be transmitted to a data storage area. A DSP processes the digitized data, e.g., the DSP may subtract background from the samples and may identify the start of a pulse using a form of threshold detection such as that described below. The DSP may also integrate the area under the digital signal to provide a number which represents the magnitude of the detected light (i.e., scattered light or emitted light).

In addition, more than one DSP may be used to process the data. For example, an additional DSP may be configured to perform processing activities that often take considerable time such as time consuming digital filtering (i.e., standard finite impulse response filtering or "FIR") and/or any various waveform analysis procedures that are often employed to improve the quality of data extracted in the presence of noise.

Figure 2:
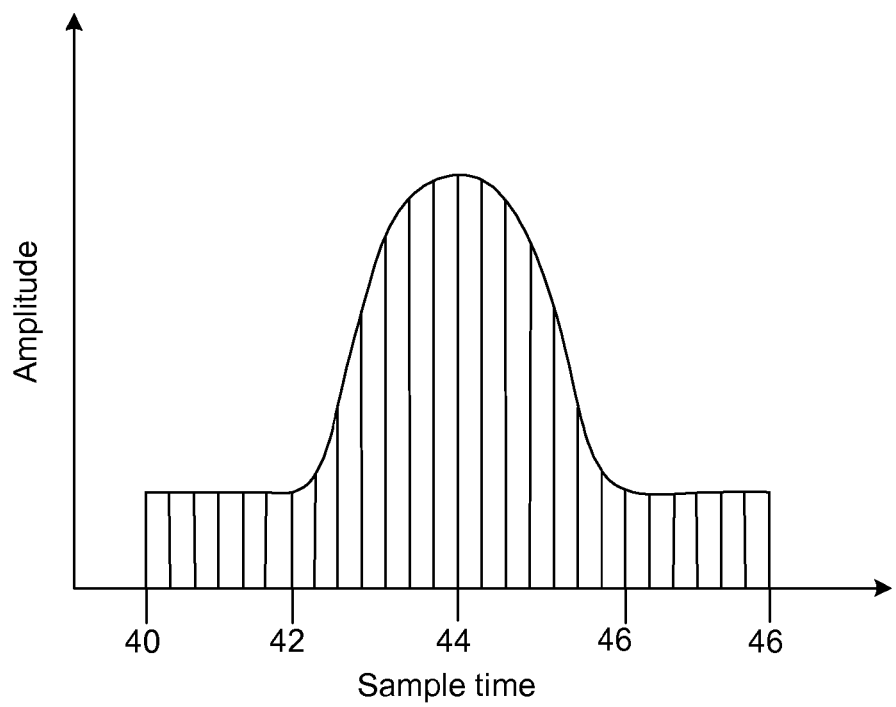
FIG. 2 is a graph illustrating one example of a pulse that is substantially symmetrical about a peak value.

FIG. 2 illustrates one example of a plurality of sample values that may be generated over time. The plurality of sample values include samples taken during an event and samples that are not taken during an event. Sample values that correspond to an event and that are taken successively in time may define a single pulse. The single pulse, therefore, corresponds to a single event. In the case of flow cytometry, the event may be defined as the illumination of a microsphere. The samples that are not taken during an event may have values that are approximately equal to a baseline value. These sample values may, however, be larger or smaller than the baseline value depending on, for example, aberrations in the sample or sheath fluid. In the example shown in FIG. 2, the sample values that do not represent an event may include sample values taken between times 40 and 42 and times 46 and 48. The number of sample values that do not represent an event may vary depending upon, for example, the sampling frequency of the measurement device, the flow rate of the sample fluid, and the spacing between microspheres.

The samples that are taken during an event may have values that are greater than the baseline value. In the example shown in FIG. 2, the sample values that correspond to an event may include the samples taken between times 42 and 46. In some embodiments, the samples that correspond to an event are determined by comparing the values of the samples to a threshold value. If the sample values are above the threshold value, then the samples may be determined as corresponding to an event. If the sample values are below the threshold value, then the samples may be determined as not corresponding to an event.

For example, for purposes of analysis, an event may be defined by the user with respect to a minimum datum criterion, for example, when the signal-to-noise (S/N) ratio is equal to a threshold value of about 2 or 3, or another threshold value. The S/N threshold value may be increased or decreased to compensate for the degree of purity of the samples (for example, whether integrity of the microspheres is high, or whether many of the microspheres have crumbed into smaller entities) and/or the purity of the fluid, or to compensate for any other situation (for example, bubbles) affecting background noise in the cytometric or other flow measurement readings, or in readings from any other measurement device. In effect, the S/N threshold may be adjusted to reflect the range of anticipated small signal amplitudes, particularly including amplitudes of background signals. In addition, more significant S/N threshold strategies can be used. The DSP reads the data and determines whether the data reach the user selected S/N threshold so as to warrant processing by the DSP.

FIG. 2 illustrates an ideal or expected event with a Gaussian distribution of amplitude with respect to time. The peak of a pulse is determined by comparing sample values within the pulse and determining the largest sample value. The largest sample value is then designated as the peak value. In the example, shown in FIG. 2, the sample value taken at time 44 has the largest value and would therefore be designated as the peak value according to this method. Such a method also usually includes summing a number of sample values taken before and after this peak value. The number of sample values on each side of the peak value that are summed may be approximately equal to half the number of samples expected in the pulse. For example, if it is expected that about 13 samples will be taken during an event, then 6 sample values on both sides of the peak value may be summed. In this manner, the sum of approximately all of the sample values corresponding to a single pulse may be determined.

The event shown in FIG. 2 is approximately symmetrical about the peak value. Therefore, the above-described method for determining the pulse peak and the sample values to be summed would produce a sum that accurately reflects the pulse. However, if the pulse includes noise such as a noise spike in the vicinity of the pulse, then the peak of the pulse may not be identified correctly. For example, the sample data shown in FIG. 3 includes a noise spike at time 56. Although the noise spike is shown to be located in a leading portion of the pulse, it is to be understood that noise spike may occur anywhere within the sample data (e.g., near a central portion of the pulse, near a trailing edge of a pulse, or within baseline data on either side of the pulse). In addition, more than one noise spike may occur within the sample data. Furthermore, although the pulses shown in FIGS. 2 and 3 have generally Gaussian shapes, it is to be understood that the pulses may have any shape or probability distribution known in the art.

Figure 3:
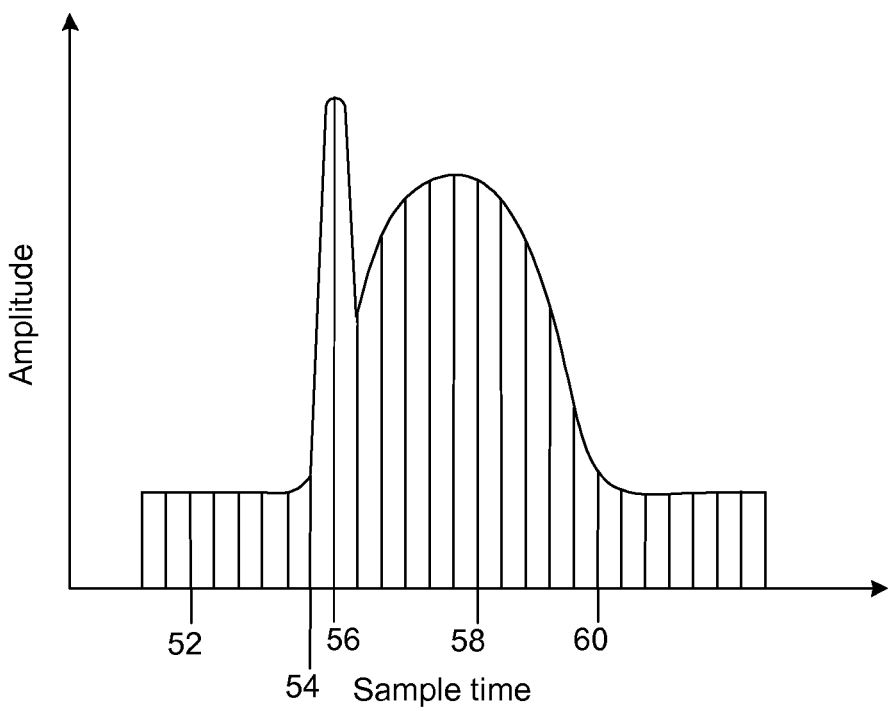
FIG. 3 is a graph illustrating one example of a pulse that includes a noise spike.

If a peak search is performed on the sample data shown in FIG. 3 as described above (i.e., searching for the largest sample value), then the sample value taken at time 56 would be identified as the peak value. If the method described above in connection with FIG. 2 is used to determine a sum of the sample values in the pulse, a number of samples of both sides of the noise spike would be added (e.g., 6 sample values on both sides of the noise spike). Therefore, the samples that are used to find a sum for the pulse would include sample data that is taken between times 52 and 54. As such, the sample data that is used to find a sum for the pulse includes sample data that is actually representative of baseline data not the event. As such, this method may produce inaccurate sums when noise is present in the sample data.

The preferred embodiments include several computer-implemented methods to reduce the susceptibility of a peak search to signal noise by scanning for the largest sum rather than the largest sample value. For example, one embodiment may include selecting a value N, and computing a running sum for N values. N may be chosen such that it is slightly larger than the number of samples expected in the widest pulse. For example, if the widest pulse is expected to include 13 samples, N may be 15, 17, etc. As each sample is obtained, a sum of N samples (i.e., the current sample and the previous N−1 samples) may be determined. In this manner, a running sum of N samples may be updated as the samples are taken. When a sufficient number of samples have been processed, the array of sums is scanned for a peak or the largest sum value. A sufficient number of samples may be, for example, a number of samples expected in the pulse and twice the number of samples expected between the pulse and successive pulses. Alternatively, a sufficient number of samples may be any number larger than N (e.g., 2N, 3N, etc.). In either case, the number of samples that are processed should be large enough to account for variation in timing of the event (e.g., variation in the flow rate of the sample, etc.).

The peak sum may be determined as the sum that has the largest value. The peak sum may then be designated as the sum for the pulse. Therefore, this method may reduce the noise sensitivity of a peak search by looking for the peak sum rather than an individual peak sample. For example, if this method is used to process the sample data shown in FIG. 3, the peak sum may be determined as the sum of the sample values taken between times 54 and 60. As such, the sample data that is used to find a sum for the pulse includes sample data that is actually representative of the event and does not includes sample data that is representative of the baseline data. Even though the sample data that is used to find the sum includes noise (e.g., the noise spike at time 56), this method will be substantially more accurate than a sum that is based on the largest peak value instead of the largest sum. The sum is a measure of the light scattered or emitted by a microsphere. Therefore, the sum may be used to determine an identity of the microsphere, a size of the microsphere, and/or an identity of a reaction taking place on the surface of the microsphere. Determining the sum of the pulse using the largest sum instead of the largest peak value may also improve the coefficient of variation (CV) for the measurements.

Figure 4:
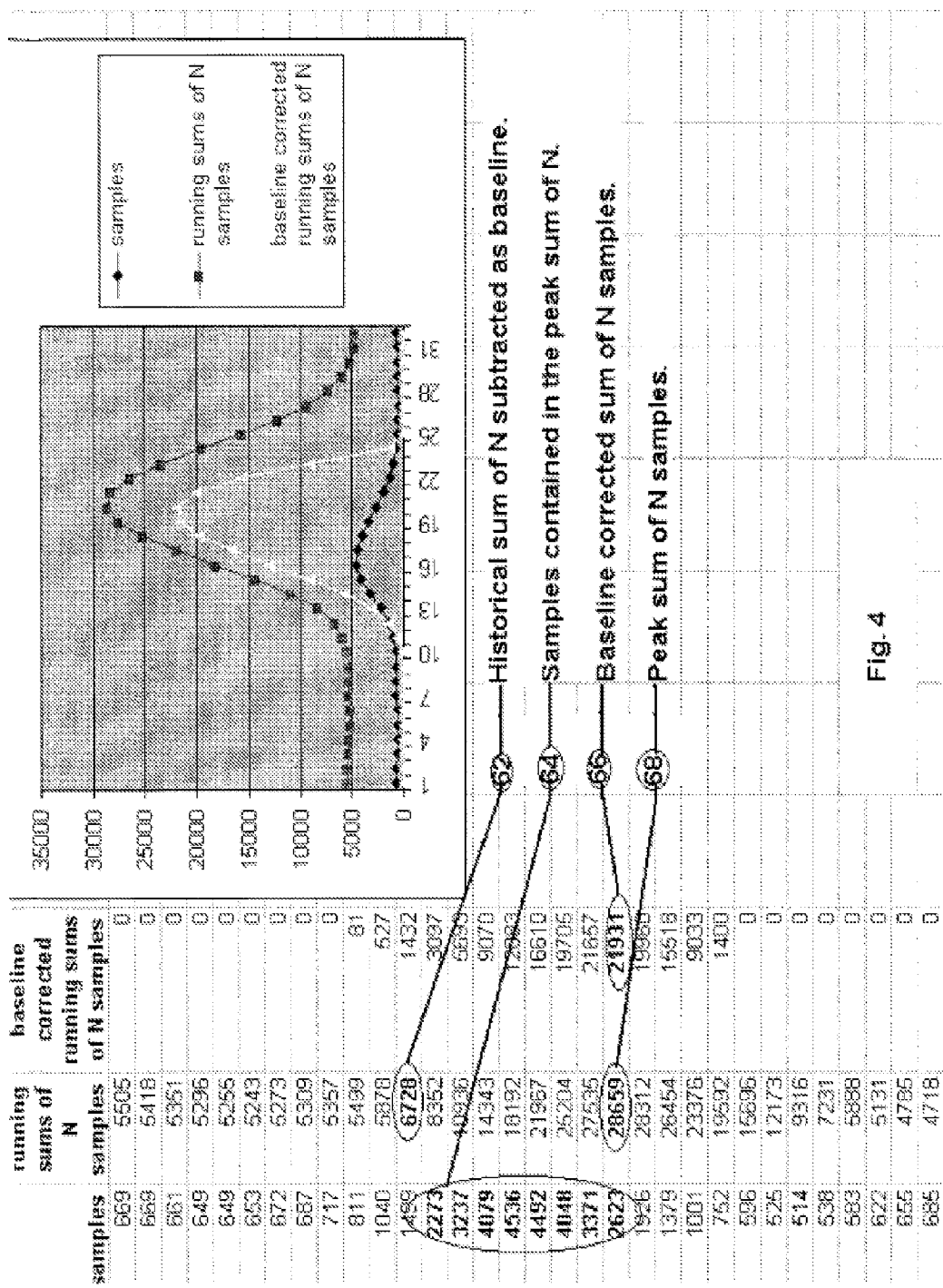
FIG. 4 is a spreadsheet with a graph insert showing samples, running sums of N samples, and a baseline corrected running sum of N samples.

Another improvement is that, in one embodiment, baseline correction may be performed by maintaining a historical record of a sufficient number of running sum of N values immediately preceding the peak running sum of N value, such that one of the historical running sum of N values composed entirely of baseline samples preceding the oldest sample contained in the peak running sum of N value can be subtracted from the peak running sum of N value to produce a baseline corrected peak running sum of N value. For example, in FIG. 4, the peak running sum of N, (68) is composed of 8 samples (64). The baseline running sum of N (62) is composed of the 8 samples immediately preceding those in the peak running sum of N (64). The baseline running sum of N (62) is subtracted from the peak running sum of N (68) to produce the background corrected running sum of N (66). FIG. 4 also shows pictorially why the preferred embodiment would include the ability to select both the number of samples to be contained in the running sums of N, and sample point at which the baseline running sum of N is computed. The running sums of N should contain enough samples to completely enclose the peak, and the baseline running sum of N should be shifted sufficiently before the peak to contain only baseline samples.

In contrast, in some currently used baseline correction methods, a weighted average of non-pulse samples is used to correct the baseline. One example of such a baseline correction method is illustrated in U.S. Pat. No. 5,067,090 to Seeman, which is incorporated by reference as if fully set forth herein. The weighted average attempts to smooth baseline noise at the cost of responsiveness to current baseline transients.

Program instructions implementing methods such as those described above may be transmitted over or stored on a carrier medium. The program instructions may be executable on a computer system to perform any of the computer-implemented methods described herein. In some embodiments, the program instructions may include one or more algorithms that are configured to perform one or more of the computer-implemented methods described herein. One example of program instructions that may be used to perform one of the computer-implemented methods described above is illustrated in the Appendix, which is filed herewith and which is incorporated by reference as if fully set forth herein. This programming code may be included with other program instructions for the DSP. The carrier medium may be a transmission medium such as a wire, cable, or wireless transmission link, or a signal traveling along such a wire, cable, or link. The carrier medium may also be a storage medium such as a read-only memory, a random access memory, a magnetic or optical disk, or a magnetic tape.

It will be appreciated to those skilled in the art having the benefit of this disclosure that this invention is believed to provide various computer-implemented methods for analyzing data generated by a flow cytometer based measurement system. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A method of mitigating noise in the analysis of digital samples including an event, comprising:
    illuminating one or more particles in a flow tube;
    detecting output signals generated from said illumination of a particle;
    sampling said output signals as a function of time;
    grouping a number of sample values into a subset and creating a plurality of subsets over time;
    summing the sample values in each subset to determine a sum for each subset;
    comparing the sum for each subset to the sums for each other subset; and
    designating the greatest sum as the sum for the event, wherein said designating mitigates noise in the analysis of the digital samples for the event.

2. The method of claim 1, wherein each subset comprises N sample values and wherein N is equal to or greater than the number of samples expected during an event.

3. The method of claim 1, including correcting the baseline of sample values not associated with an event by subtracting a sum of at least 1.5 N samples before the greatest sum.

4. The method of claim 1, including writing the digital sample values to a database.

5. The method of claim 1, including using the greatest sum to determine the identity of the particle corresponding to the event.

6. The method of claim 1, including using the greatest sum to determine the surface reaction on a particle surface.

7. A flow cytometer for examining a stream of particles comprising:
    a light source configured for illuminating a particle in said stream;
    a light detector disposed to collect samples of said particle illumination over time and to create digital sample values representing said illumination samples; and
    a signal processor which creates groups of sample values, determines a sum for each group, compares the sum of each group to the sums of each other group, and designates the greatest sum as the peak sum for the particle illumination, wherein the greatest sum mitigates noise in the examining of the sample values for the particle illumination.

8. The flow cytometer of claim 7, wherein the detector is configured for outputting a current proportional to the light scattered by said particle.

9. The flow cytometer of claim 7, including a plurality of light detectors to detect fluorescence of different wavelengths.

10. The flow cytometer of claim 7, including a database for recording said digital sample values.

11. The flow cytometer of claim 7, wherein said processor is programmed to create groups of N sample values and wherein N is equal to or greater than the number of samples expected during said particle illumination.

12. A method of data processing, comprising:
    collecting a number of digital sample values;
    grouping a plurality of successive sample values into a first set;
    summing the sample values of the first set to create a first sum;
    grouping a plurality of successive sample values into a second set;
    summing the sample values of the second set to create a second sum;
    comparing said first and second sums; and
    designating the greatest sum as an event sum, wherein said designating mitigates noise in analysis of the digital sample values for the event.

13. The method of claim 12, including repeating said grouping, summing, and comparing steps for N sets of sample values.

14. The method of claim 13, including correcting the baseline of sums of samples by maintaining a historical record of sums of sets and identifying a sum which does not contain an event.

15. The method of claim 12, including processing said event sum as an indication of the light scattered by a particle in a flow cytometer.

16. The method of claim 12, including processing said event sum as an indication of the light emitted by a particle in a flow cytometer.

* * * * *